United States Patent
Marx et al.

(10) Patent No.: US 9,506,024 B2
(45) Date of Patent: Nov. 29, 2016

(54) CIRCULATION SYSTEM

(75) Inventors: Uwe Marx, Spreenhagen (DE); Gerd Lindner, Berlin (DE); Reyk Horland, Berlin (DE); Silke Hoffmann, Berlin (DE); Roland Lauster, Berlin (DE)

(73) Assignee: TISSUSE GMBH, Berlin (DE)

( * ) Notice: Subject to any disclaimer, the term of this patent is extended or adjusted under 35 U.S.C. 154(b) by 0 days.

(21) Appl. No.: 13/814,673

(22) PCT Filed: Aug. 5, 2011

(86) PCT No.: PCT/EP2011/003940
§ 371 (c)(1),
(2), (4) Date: Apr. 8, 2013

(87) PCT Pub. No.: WO2012/016711
PCT Pub. Date: Feb. 9, 2012

(65) Prior Publication Data
US 2013/0295598 A1    Nov. 7, 2013

Related U.S. Application Data (60) Provisional application No. 61/371,368, filed on Aug. 6, 2010.

(30) Foreign Application Priority Data

Aug. 6, 2010    (EP) .................................. 10008244

(51) Int. Cl.
*C12M 1/12*    (2006.01)
*C12M 3/00*    (2006.01)
(Continued)

(52) U.S. Cl.
CPC ............. *C12M 21/08* (2013.01); *C12M 23/16* (2013.01); *C12M 25/10* (2013.01); *C12M 25/14* (2013.01); *C12M 29/08* (2013.01); *C12M 29/16* (2013.01); *C12N 5/0691* (2013.01)

(58) Field of Classification Search
CPC .... C12M 21/08; C12M 23/16; C12M 25/10; C12M 25/14; C12M 29/08; C12M 29/16; C12N 5/0691
USPC ......................................... 435/29, 303.1, 366
See application file for complete search history.

(56) References Cited

U.S. PATENT DOCUMENTS

2002/0182241 A1* 12/2002 Borenstein et al. .......... 424/422
2004/0203147 A1    10/2004 Triffitt et al.
(Continued)

FOREIGN PATENT DOCUMENTS

DE    4218917    12/1993
JP    2002542883    12/2002
WO    00/66036 A2    11/2000

OTHER PUBLICATIONS

International Search Report for PCT/EP2011/003940. Completed by the European Patent Office on Nov. 7, 2013, 3 Pages.
(Continued)

*Primary Examiner* — Michael Hobbs
(74) *Attorney, Agent, or Firm* — Brooks Kushman P.C.

(57) ABSTRACT

A self-contained circulation system, which supports the formation of capillaries in capillary growth sections and allows the formation of micro organoids and/or micro tissue sections for monitoring the effect of one or more test compounds and determining efficacy, side-effects, biosafety, metabolites, mode of action or organ regeneration as well as methods of establishing such micro organoids and/or micro tissue in the self-contained circulation system.

21 Claims, 4 Drawing Sheets

(51) Int. Cl.
   *C12M 3/06*   (2006.01)
   *C12M 1/00*   (2006.01)
   *C12N 5/071*  (2010.01)

(56) References Cited

U.S. PATENT DOCUMENTS

2004/0254514 A1* 12/2004 Gura .................. 604/5.01
2007/0224677 A1   9/2007 Neumann
2009/0191631 A1   7/2009 Bornemann

OTHER PUBLICATIONS

Intaglietta et al. Cardiovascular Research 1996, vol. 32, p. 632-643, "Microvascular and tissue oxygen distribution."
Dongeun et al. Science 2010, vol. 328, p. 1662-1668, "Reconstituting Organ-Level Lung Functions on a Chip."
Giese et al. Journal of Biotechnology 2010, vol. 148, p. 38-45, "Immunological substance testing on human lymphatic micro-organoids in vitro."
Catapano et al. Topics in Tissue Engineering 2007, vol. 7, Chapter 8, 42 Pages, "Bioreactors for Liver Tissue Engineering."
Schanz et al. Journal of Biotechnology 2010, vol. 148, p. 56-63, "Vascularised human tissue models: A new approach for the refinement of biomedical research."
Song et al. Anal. Chem. 2005, vol. 77, p. 3993-3999, "Computer-Controlled Microcirculatory Support System for Endothelial Cell Culture and Shearing."
Sonntag et al. Journal of Biotechnology 2010, vol. 148, p. 70-75, "Design and prototyping of a chip-based multi micro-organoid culture system for substance testing, predictive to human (substance) exposure."
Tanaka et al. Lab Chip 2006, vol. 6, p. 362-368, "An actuated pump on-chip powered by cultured cardiomyocytes."
Straube et al. Artificial Organs 2006, vol. 30, No. 10, p. 743-755, "Reversibility of the Differentiated State: Regeneration in Amphibians."
Zhang et al. Lab Chip 2009, vol. 9, p. 3185-3192, "Towrds a human-on-chip: Culturing multiple cell types on a chip with compartmentalized microenvironments."
Zhang et al. Biomaterials 2009, vol. 30, p. 3847-3853, "The controlled presentation of TGF-B1 to hepatocytes in a 3D-microfluidic cell culture system."
Zhang et al. Biomaterials Jul. 2009, vol. 30, No. 19, p. 3213-3223, "Dynamic Culture Conditions to Generate Silk-Based Tissue-Engineered Vascular Grafts."
Edited by O'Neil et al. 2006, the Merck Index—An Encyclopedia of Chemicals, Drugs, and Biologicals (14th Edition, Version 14.9) 4 Pages, Website http://www.knovel.com/web/portalibrowse/display?_EXT_KNOVEL_DISPLAY_bookid=1863.

* cited by examiner

CIRCULATION SYSTEM

CROSS-REFERENCE TO RELATED APPLICATION

This application is the U.S. national phase of PCT Application. No. PCT/EP2011/003940 filed on Aug. 5, 2011, which claims the benefit of U.S. provisional application 61/371,368 filed on Aug. 6, 2010, and claims priority to European Patent Application No. 10 008 244.5 filed on Aug. 6, 2010, the disclosures of which are incorporated in their entirety by reference herein.

INTRODUCTION

This invention concerns a self-contained circulation system, which supports the formation of capillaries in capillary growth sections and allows the formation of micro organoids and/or micro tissue sections for monitoring the effect of one or more test compounds and determining efficacy, side-effects, biosafety, metabolites, mode of action or organ regeneration as well as methods of establishing such micro organoids and/or micro tissue in said self-contained circulation system.

BACKGROUND

Enormous efforts have been made to develop circulation systems for physiological nutrient supply and waste removal of in vitro cultured tissues. These developments are aiming for in vitro generation of organ equivalents such as liver, lymph nodes (Giese et al., 2010, Journal of Biotechnology 148, 38-45) and lung (Huh et al., 2010, Science, (328) 5986, pp. 1662-1668) or even multi-organ systems (Sonntag et al, 2010, Journal of Biotechnology 148, 70-75) for substance testing, research on organ regeneration or for transplant manufacturing. Initially technical perfusion systems based on membranes, hollow fibres (Catapano and Gerlach. Bioreactors for Liver Tissue Engineering. 2. Topics in Tissue Engineering, Vol. 3, 2007. 1-42 Eds. N Ashammakhi, R Reis & E Chiellini) or networks of micro channels (Du et al., Chapter 7: Microfluidic Systems for Engineering Vascularized Tissue Constructs". 2008 (Book chapter)) were used for these purposes.

In a liver support system developed by Gerlach and co-workers three bundles of hollow-fibres are cross-woven with each other, forming multiple identical micro culture spaces for plasma perfusion and oxygen supply. Human plasma perfusion is assured by two micro-filtration hollow fibre membrane bundles, whereas oxygenation takes place through a liquid-impermeable oxygen transport membrane. Liver support systems based on this principle have well-performed over several weeks, being included in a plasma flow circuit of patients.

Du et al. summarised fluidic platforms for generating micro-vascularised tissue constructs on the basis of hydrogels and micro-fabrication techniques. The overview highlights the technical ability to form blood-capillary-network like channel structures within polymeric materials for efficient liquid perfusion through tissue cultures. The majority of the resulting micro systems were used for highly efficient technical perfusion not including endothelial cells.

Such systems are limited to the use of culture media or plasma, but do not allow for whole blood perfusion due to clotting phenomena. In addition they do not provide the natural blood tissue barrier, which in vivo is composed by closed endothelial cell layer. This allows for active transport through the cell layer, as well as for signalling from the tissue into the capillary network. Different approaches were developed to line technical perfusion systems (Song et al., 2005, Anal. Chem., 2005, 77, 3993-3999) or synthetic or biological matrices (Zhang et al., 2009, Biomaterials, 30(19): 3213-3223; Walles, 2010, Journal of Biotechnology 148, 56-63) up with endothelial cells.

Song and co-workers developed a micro circulatory support to culture endothelial cells under defined shear stresses. Closed monolayers of endothelial cells could be established in individual cell culture compartments, located between technical transport channels.

To generate tissue-engineered vascular grafts (TGVG) Zhang et al. developed a tissue engineered construct that mimicked the structure of blood vessels using tubular electrospun silk fibroin scaffolds with suitable mechanical properties. They seeded human coronary artery smooth muscle cells (HCASMCs) and human aortic endothelial cells (HAECs) onto the luminal surface of the tubular scaffolds and cultivated under physiological pulsatile flow, which was generated within the dual loop bioreactor using external tubing and pumps.

A fully biological matrix for the establishment of an endothelialised vasculature in vitro was used by Walles et al., connecting polymeric tubing and controlled pumping system to an acellularised animal gut segment. In this system the capillaries which are entirely covered by endothelial cells are limited to the functionally relevant areas of the biomatrix.

However, none of the prior art circulation systems was suitable for long-term tissue culture based on whole blood as provided in this application.

The present invention relates to a closed and self-contained circulation system emulating the natural blood perfusion environment of vertebrates at tissue level. The system uses a miniaturised physiological blood circulation to provide circulation of micro liter volume to support milligrams of tissue. This mimics the physiological ratio of humans, where liters of blood-volume support kilograms of tissue at a chip-compatible micro scale. The self-contained circulation system contains at least one capillary growth section located between the micro inlets and micro outlets of the system.

A capillary growth section for formation of blood capillaries, supporting nutrient exchange, is integrated into the circulation, in addition to a miniaturised pump and transport channels.

BRIEF SUMMARY OF THE INVENTION

In a first aspect the present invention relates to a circulation system (1), which is self-contained and comprises:
  a. at least one capillary growth section (2), comprising at least two micro inlets (3) and two micro outlets (4),
  b. a directional pumping device (5), and
  c. an arteriolar transport channel (6) connecting the directional pumping device (5) and the at least two inlets (3) and a venular transport channel (7) connecting the directional pumping device (5) and the at least two outlets (4).

In a second aspect the present invention relates to a method circulation system (1) of the invention, comprising the steps of
  a. seeding endothelial cells into the circulation system (1), and
  b. incubating at least until capillaries (14) have formed in the capillary growth section (2) and/or until an endothelial cell layer has formed in the transport channels and/or until an endothelial cell layer has covered all inner surfaces of the pumping device (5).

In a third aspect the present invention relates to a circulation system (1) producible by the method of the present invention.

In a fourth aspect the present invention relates to the use of the circulation system (1) according to the present invention or producible according to the present invention for monitoring the effect of one or more test compounds and/or for determination the efficacy, side-effects, biosafety, metabolites, mode of action or organ regeneration.

DETAILED DESCRIPTION OF THE INVENTION

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Preferably, the terms used herein are defined as described in "A multilingual glossary of biotechnological terms: (IUPAC Recommendations)", Leuenberger, H. G. W., Nagel, B. and Klbl, H. eds. (1995), Helvetica Chimica Acta, CH-4010 Basel, Switzerland) and as described in "Pharmaceutical Substances: Syntheses, Patents, Applications" by Axel Kleemann and Jurgen Engel, Thieme Medical Publishing, 1999; the "Merck Index: An Encyclopedia of Chemicals, Drugs, and Biologicals", edited by Susan Budavari et al., CRC Press, 1996, and the United States Pharmacopeia-25/National Formulary-20, published by the United States Pharmcopeial Convention, Inc., Rockville Md., 2001.

Throughout this specification and the claims which follow, unless the context requires otherwise, the word "comprise", and variations such as "comprises" and "comprising", will be understood to imply the inclusion of a stated feature, integer or step or group of features, integers or steps but not the exclusion of any other feature, integer or step or group of integers 15 or steps. In the following passages different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

In the following, some definitions of terms frequently used in this specification are provided. These terms will, in each instance of its use, in the remainder of the specification have the respectively defined meaning and preferred meanings:

"Cells" means cell lines or primary cells of vertebrates or invertebrates.

"Organoids" means artificial, de novo generated, functional cell aggregates of different types of cells in vitro that show at least one organ or tissue function, preferably shows the majority of or essentially all organ or tissue functions.

"Tissues" stands for biopsy material or explants taken from patients or animals or in vitro generated tissues.

"Differentiation" means the development of tissue specific functions of cultured cells.

"Maintenance" describes the ability to keep all functions of a given tissue constant within a given cell culture process, preferably without significant signs of cell death and/or apoptosis.

"Medium" (plural form: "media") means growth supporting liquid with nutrients and substances for cultivation of cells. Examples of suitable media comprise DMEM, Ham's F12 and RPMI.

"Matrix" means substances or mixtures of substances, which maintain viability, enhance proliferation, differentiation, and function of cells and/or organoid or organ formation. Matrix material is preferably provided in a form which can be fitted to file the space of the capillary growth section (2). Matrixes usable in the context of the present invention can take a variety of shapes comprising, e.g. hydrogels, foams, fabrics or nonwoven fabrics. The matrix material may comprise naturally occurring matrix substances like extracellular matrix proteins, preferably collagens, laminins, elastin, vitronectin, fibronectin, small matricellular proteins, small integrin-binding glycoproteins, growth factors or proteoglycans or may include artificial matrix substances like non degradable polymers such as polyamid fibres, methylcellulose, agarose or alginate gels or degradable polymers, e.g. polylactid.

"Inner surface" means those surfaces of the circulation system (1), which are in direct contact with the circulating media, plasma and/or blood, e.g. whole blood.

To overcome the problems associated with prior art cell culturing systems, the present invention provides a circulation system (1), which is self-contained and comprises:
  a. at least one capillary growth section (2), comprising at least two micro inlets (3) and two micro outlets (4),
  b. a directional pumping device (5), and
  c. an arteriolar transport channel (6) connecting the directional pumping device (5) and the at least two inlets (3) and a venular transport channel (7) connecting the directional pumping device (5) and the at least two outlets (4).

"Self-contained" refers to the fact that the fluid in the system is circulated within the system," i.e. between the directional pumping device (5) the capillary growth section (2) or sections, and that preferably there is no fluidic connection for continuously providing fluid, e.g. medium, blood, from an external fluid reservoir into the circulation system (1). "External" in this context means that the fluid reservoir is not an integral part of the circulation system, e.g. is connected via tubing to the circulation system.

If substances, e.g. nutrients and/or fluids, have to be replenished during the course of incubation it is preferred that such nutrients or fluids are supplied discontinuously through an injection port (17), which is preferable located in an arteriolar or venular transport channel or connected to the capillary growth section. In the former case the substances, e.g. nutrients and/or fluids, are directly injected into the interior of the capillaries. This injection potentially leads to injury of the endothelial cells lining the opening of the injection port (17) on the inner surface of the circulation system (1). In the later case the injection increases the fluid pressure in the extracapillary space around the capillaries formed in the capillary growth section. Fluids and nutrients will dissipate into the circulation through the capillaries due to the increased partial pressure in the extra capillary space. To avoid an increase in the pressure in the system over time and with repeat injections of substances to be replenished, it is preferred that the circulation system further comprises a pressure compensating reservoir. If the injection port (17) is arranged to allow injection into the interior of the capillaries, it is preferred that the pressure compensating reservoir is connected to the extracapillary space. Conversely, if the injection port (17) is arranged to allow injection into the extracapillary space, it is preferred that the pressure compensating reservoir is connected to the interior or the capillaries. In some preferred embodiment the pressure compensating reservoir has an opening, preferably a small bore hole or a one way valve, to release gas from the pressure compensating reservoir. This opening is preferably configured in a way to only release gas into the surrounding, if a set threshold pressure is reached. Suitable means are, e.g. spring loaded one-way valves or silicon plugs with a slit. By this means it is possible to prevent over pressurising the circulation system, which may damage the capillary formed. Given the small total liquid volumes comprised in the system, it is preferred that very small volumes, e.g. less then 10% of the total volume are injected at any given time. The preferable method to load fluids and/or cells into the circulation is the introduction of an injector, preferably an injection needle, into the injection port and to injection fluids and/or cells into the circulation by an injector movement speed adjusted to the movement speed of endothelial cells. This is particularly preferred once a closed endothelial cell monolayer has been formed. It is preferred that the injection port is self-sealing, i.e. closes liquid and preferably also air tight once the injection-device, e.g. syringe, has been withdrawn. Examples of such self-sealing injection ports are well known in the art and include, one-way valves and silicon plucks.

In preferred embodiments the injection port (17) and/or the pressure compensating reservoir is separated from the circulation or the extracapillary space by a cell retention membrane, i.e. a membrane having an average pore size smaller than the average size of the cells growing in the circulation system (1) of the invention or by cell exclusion channels, which are sized to exclude the cells growing in the circulation system (1) of the invention to prevent clogging or escape of cells.

It is possible that gas is co-injected with fluids either during the initial filling of the system or during later injections. To avoid blockage of the circulation by trapped gas bubbles, it is preferred that one or more traps for gas bubbles are provided in the circulation system (1). Such traps may have the form of cavities or notches on the upward-facing side of an arteriolar or venular transport channel.

Additionally, it is preferred that gaseous medium, e.g. $O_2/CO_2$, is provided to the capillary growth section (2) in a passive manner, e.g. by diffusion into the capillary growth section (2) through a gas permeable biocompatible matrix (8) and/or through the arteriolar transport channels (6).

It is one advantage of the circulation system (1) that it is possible to maintain two or more different tissues and/or organoids (15) within one self-contained system, which are perfused by the same circulating fluid and, thus, are in fluidic connection as in the natural environment. The number of capillary growth sections (2) is generally determined by the number of separate tissues and/or organoids (15) to be maintained. Thus, in a preferred embodiment of the circulation system (1) of the present invention the circulation system (1) comprises at least two capillary growth sections (2); preferably it comprises 3, 4, 5, 6, 7, 8, 9 or 10 capillary growth sections (2).

The exchange of gases, e.g. of $O_2/CO_2$ is preferably effected by providing gas permeable alveolar and venular transport channels (7), i.e. the alveolar and venular transport channels comprise or consists of a gas permeable material. Depending on the total fluid volume in the system and the total surface area of the transport channel (5, 6) the perfusion of $O_2/CO_2$ through the inner surface of the transport channels may not be sufficient to maintain the cells and/or organoids (15) in the circulation system (1). In these cases it is preferred that the material of one of the capillary growth section (2) is at least in part gas permeable and thereby functions as a "micro-lung" supplying $O_2$ to the entire circulation system (1). Accordingly, it is preferred that one or more walls of the capillary growth section comprise or consist of a gas permeable material. Suitable gas permeable materials are known in the art. Preferably, the material that is used to form one or more walls of the capillary growth section is polydimethylsiloxane (PDMS).

The capillary growth section (2) is a space that is provided for assembly of capillaries (14) by endothelial cells and optionally smooth muscle cells that are seeded into the system. The capillary growth section is preferably filled with a matrix (8) which serves the purpose of providing a growth scaffold for the capillaries (14) which are formed naturally once endothelial cells are seeded into the system and fluid is circulated through the capillary growth section (2). It is, thus, preferably that the biocompatible matrix (8) comprises micro channels, structures and/or networks, which allow and support formation of capillaries (14) by endothelial cells. Preferably, these structures themselves do not have the shape of the later capillaries but merely provide attachment points and/or guidance for the capillaries formed. It is preferred that the capillary growth section (2) comprises or consists of a semi-solid, biocompatible matrix (8). Once endothelial cells are seeded into the system the capillaries (14) will start to form typically beginning at the micro inlets (3) and will grow directed by the fluid flow to eventually connect with one of the micro outlets (4). Alternatively, biocompatible hollow fibres (9) are provided either alone or embedded in a biocompatible matrix (8) as set out above. These are preferably connected at one side to the micro inlet and at the other side to the micro outlet (4), thereby guiding the growth of the endothelial cells. To maintain the elasticity of the resulting capillaries (14) it is preferred that the material of the biocompatible hollow fibre (9) is biodegradable; since this allows its removal over time once the capillary has formed.

Preferably the biocompatible matrix (8) comprises or consists of matrigel, fibrin gel, agarose gel, alginate gel, synthetic gel, cross-linkable polymers and the biocompatible hollow fibre (9) preferably consists of a material selected from the group consisting of polylactic acid (PLA), polylactide-co-glycolide (PLGA), polycaprolactone (PCL) and poly(fumaric-cosebacic anhydride, polyvinyl alcohol, acrylic acid ethylene co-polymer, polyacrylic acid, polyglycolide, polylactide, cellulose derivatives, carbomethoxy/ethyl/hydroxypropyl, hyaluronic acid, folate linked cyclodextrin/dextran, sarcosine/amino acid spaced polymer, carrageenan, pectin/chitosan, chitosan, dextran, collagen or mixtures thereof. Preferred crosslinkable polymers are PEG derivatives of the formula PEG-(DCR-CG)n, where PEG is poly(ethylene glycol), DCR is a degradation control region, CG is a cross-linking group, and n is equal to or greater than 3. Particularly preferred materials for the biocompatible hollow fibre (9) are PLA and PLGA.

The choice of the materials of the matrix and/or hollow fibre as well as of the arteriolar or venular transport channels ascertains that the inner surface of the circulation system of the invention is rapidly and completely covered with endothelial cells.

Analysis of oxygen transport has led to the concept that the tissue site most distant from the inflow end of the capillary builds a lethal corner (Intaglietta et al, 1996, Cardiovascular Research 32, 632-643). As areas of low $O_2$ partial pressure are also present in the body, e.g. in tumour tissue, it is an aim of the present invention to establish a so-called "neovascularisation" region (16) within the capillary growth section (2), i.e. a section wherein no capillaries (14) are formed during the initial establishment of the capillaries (14) in the circulation system (1) of the present invention. This is achieved by providing a sub-section (16) within the capillary growth section (2) that is devoid of micro inlets (3) and outlets (4). If this sub-section (16) is sufficiently far removed from corresponding micro inlets (3) and micro outlets (4) the formation of capillaries (14) is impaired in this sub-section. The subsection is sufficiently far removed, if no capillaries are formed therein, preferably it is removed at least 100 µm and up to 500 µm preferably the subsection has a distance from the micro inlets (3) and/or micro outlets in the range of 100 µm to 300 µm. It is then possible to place any tissue or organoid of choice in this area, e.g. tumour tissue, to investigate the cues for building of capillaries (14) or regeneration processes. As outlined in more detail below it is preferred that one part of the material delimiting the capillary growth section (2) can be removed to allow access to the capillary growth section (2). It is envisioned that cells and/or organoids are introduced through this opening into the capillary growth section (2). Afterwards the opening is covered to be fluid tight. The material of the cover is preferably selected from translucent materials, e.g. glass or plastic, which allow microscopic inspection of the capillary growth section (2) by microscopy. Preferably, the material is not gas-permeable. However, in the embodiment, wherein one or more capillary growth section have the function of a "micro-lung" such capillary growth sections are covered with a gas-permeable cover. Preferably, the capillary growth section (2) is molded or ground into a solid block of a given material, preferably in cuboid form. In this embodiments it is preferred that the opening is at the upper side of the block and extends over the entire surface area of the capillary growth section (2).

The formation of capillaries (14) by endothelial cells is promoted, if the area to be vascularised is not supplied with oxygen. In addition the maximum length of capillaries (14) should not exceed 4 mm, because surrounding tissues at natural densities fully consumes nutrients, especially oxygen, provided through such capillaries (14) within that distance.

Accordingly, in a preferred embodiment the distance between the micro inlets (3) and micro outlets (4) which are to be connected by newly formed capillaries (14) should not exceed this maximum distance to foster the growth of the capillaries (14). Accordingly, it is preferred that the distance between a micro inlet (3) and the nearest micro outlet (4) is in the range of 0.2 mm to 4 mm, more preferably 0.3 to 2 mm, even more preferably 0.4 mm to 1 mm preferably about 0.5 mm. The width of the capillary growth section (2) is between 0.5 mm and 1.5 mm, preferably 1.0 mm and/or the height of the capillary growth section (2) is between 0.3 to 0.7 mm, preferably 0.5 mm. The volume of the capillary growth section (2) is between 0.03 µl to 4.2 µl, preferably between 0.5 µl to 1.0 µl. The total volume of the capillary growth section (2), the arteriolar transport channels (6), the venular transport channel (7) and the directional pumping device (5) is between 1.0 µl to 100 µl, preferably between 5.0 µl to 15 µl.

To promote the growth of linear capillary connections it is preferred that each of the micro inlets (3) and micro outlets (4) are arranged at opposite ends of the capillary growth section (2). It is preferred that the capillary growth section has an essentially cuboid, preferably cubic shape. Preferably, the micro inlet and micro outlet are arranged on to opposite faces of the cuboid. The length of the cuboid is then determined by the distance between the micro inlets and micro outlets. It is particularly preferred that each micro inlet (3) is directly lined up with a corresponding micro outlet (4).

It is desired that the oxygen is provided to the capillary growth sections through the capillaries, accordingly, it is preferred that the material forming the walls of the capillary growth section has a low or no gas permeability. If, however, one or more capillary growth sections have the function of a micro-lung, these growth sections are designed as outlined above. Preferably, the wall material is selected from the group consisting of glass or plastics.

As set out above the capillaries (14) form autonomously within the capillary growth section (2) once it is seeded with endothelial cells. An important directional cue for the endothelial cells is the flow of the fluid through the system. To promote the growth of capillaries (14) of the correct size it is preferred that the diameter of the micro inlets (3) and/or micro outlets (4) is between 5 µm to 5 µm, more preferably 15 µm to 30 µm. The capillaries (14) formed have a diameter in the range of 1 to 10 µm, preferably of 5 to 6 µm. As will be set out in more detail below the number of micro inlets and micro outlets in the capillary growth section corresponds to the surface area of the arteriolar and venular transport channels. To provide sufficient oxygen to tissues the respective number of micro inlets and micro outlets are preferably distributed over the surface of the respective side of the capillary growth chamber. For the same reason the distance between two capillaries formed should not be below 30 µm. Accordingly, it is preferred that the distance between the micro inlets (3) is in the range of 30 µm to 500 µm, preferably in the range of 80 µm to 200 µm and/or that the distance between the micro outlets (4) is in the range of 30 µm to 500 µm, preferably in the range of 80 µm to 200 µm. In a preferred embodiment the micro inlets (3) and/or micro outlets (4) are arranged in one, two, three or four rows.

It is envisioned that tissues and/or organoids (15) are placed in the capillary growth section(s) (2), which will perform their natural function. Accordingly, in a preferred embodiment the capillary growth section (2) further comprises an extra-capillary fluid and/or waste collector (10). The drainage of extra capillary fluid is driven by intra-capillary pressure differences. This serves the purpose of draining fluids away from the tissues and/or organoids (15), e.g. pancreas, kidney, gut, which secrete fluids extra capillary. Preferably, the waste collector (10) is separated from the biocompatible matrix (8) and/or biocompatible hollow fibre (9) in a way, which prevents the efflux of blood cells and/or tissue or organoid cells from the capillary growth section (2). Preferably the extra-capillary fluid and/or waste collector (10) is separated from the remaining capillary growth section (2) by a cell retention membrane (11), i.e. a membrane having an average pore size smaller than the average size of the cells growing in the circulation system (1) of the invention or by cell exclusion channels, which are sized to exclude the cells growing in the circulation system (1) of the invention.

To monitor the status of the system it is preferred that one or more sensors (12) are arranged in the circulation system (1) of the invention, preferably in a alveolar and/or venular transport channel (7), in the extra capillary fluid and/or waste collector (10), and/or the directional pumping device. Sensors (11), which may be used include but are not limited to pH sensors, $pO_2$ sensors; analyte capture sensors, conductivity sensors, plasmon resonance sensors, temperature sensors, $CO_2$ sensors; NO sensors, chemotaxis sensors, cytokine sensors, ion sensors, pressure sensors, potentiometric sensors, amperometric sensors, flow-through sensors, fill sensors, impedance sensors, conductivity sensors, electromagnetic field sensors, surface acoustic wave sensors, and metabolic sensors. The sensors (12) used in this system may be sensors, which monitor the capillary growth section (2) and/or the medium flowing out of the capillary growth section (2) or may be sensors (12) located within the waste channel and/or reservoir (10).

The transport channels mimic the smaller arteries and veins in a blood system and serve as a connection between the directional pumping device (5) and the capillary growth section (2). Therefore, it is preferred that the transport channels are suitable to be coated with smooth muscle cells and endothelial cells. Transport channels of the desired diameter and form can be provided by micromachining the respective structure in a biocompatible matrix (8) or can be biocompatible hollow fibres (9). However, it is also possible to use decellularized biological arterioles and/or venules. The surface area of the transport channels (6, 7) is sufficient to provide the required 02 to most systems unless there are too many capillary growth sections (2). It is therefore preferred that said biocompatible matrix (8) or biocompatible hollow fibre (9) is at least in part gas permeable, preferably comprises or consists of PDMS. PDMS is a silicon-based organic polymer, optical clear, visco-elastic and can be directly patterned, e.g. by surface-charge lithography.

In a preferred embodiment of the invention the diameter of the arteriolar transport channel (6) and/or the venular transport channel (7) at its connection with the directional pumping device (5) is between 300 µm and 2.0 mm, preferably 500 µm. It is desirable that the speed of the fluid flow in the circulation systems (1) does not change significantly throughout 10 the system during circulation of the fluid. Preferably, the flow rate in the system is in the range of 0.02 cm/s to 0.1 cm/s, more preferably 0.03 to 0.07 cm/s most preferably about 0.05 cm/s. However, the micro inlets (3) and micro outlets (4) generally have a smaller diameter and, thus, smaller surface area than the arteriolar micro inlets (3) and venular micro outlets (4), respectively, which would lead to an increase of the flow rate when the fluid enters the 15 micro inlets (3). Accordingly, it is preferred that the arteriolar transport channel (6) branches of at least once to connect with the at least two inlets and the venular transport channel (7) branches of at least once to connect with the at least two outlets (4), respectively. To prevent significant variations of the fluid flow it is preferred that the combined cross-sectional area of the arteriolar channels after the branching point (13) is essentially identical to the cross-sectional area of the arteriolar channel in front of the branching point (13) and/or the combined cross-sectional area of the venular transport channels (7) after the branching point (13) is essentially identical to the cross-sectional area of the venular channel in front of the branching point (13). Usually, the arteriolar (6) or venular channel (7) connected to the directional pumping device (5) branches of into two or three smaller diameter arteriolar and venular channels (6, 7). The number of branching points (13) and/or the number of branches required to reduce the diameter of the arteriolar and venular channel to the diameter of the respective micro inlet (3) and micro outlet (4) is determined by the relative cross-sectional area of the arteriolar channel (6) and venular channel (7) and the diameter and cross-sectional area, respectively of the micro inlets (3) and micro outlets (4) to which they connect. If, for example, the arteriolar channel (6) has a diameter of 1 mm and the diameter of the micro inlet (3) is 50 µm than 400 micro inlets (3) have the same surface area as the arteriolar channel (6) at the directional pumping device (5). Accordingly, it is required to provide as many two-way, three-way, four-way or more branching points (13) as required to connect each individual micro inlet with a branched of arteriolar channel (6). In a preferred embodiment the branching point (13) are two-way branching points (13) and accordingly, the number of micro inlets (3) is determined by the formula $2^n$, wherein n is the number of branching points (13) in each flow path. In cases where in the circulation system (1) comprises two or more capillary growth sections (2) the flow path is branched to connect both capillary growth section (2) separately. It is not required that both branches have the same cross-sectional area in as long as the combined cross-sectional area after the branching point (13) is identical or essentially identical to the cross-sectional area in front of the branching point (13). For example, in cases where a "micro-lung" has been formed in one capillary growth section (2) it may not be required that a similar amount of fluid is directed to this organoid (15) as to the capillary growth section (2) of another organoid (15). Thus, at the branching point (13) the arteriolar branch connecting the lung-organoid will have a smaller surface area than the arteriolar branch connecting another capillary growth section (2). The combined cross-sectional area of all inlets (3) is essentially identical to the cross-sectional area of said arteriolar channel and/or arteriolar channels and the combined cross-sectional area of all outlets (4) is essentially identical to the cross-sectional area of said venular channel and/or venular channels preferably are the cross-sectional areas of arteriolar (6) and venular channels (7).

Preferably the directional pumping device (5) is a biological pump, hydraulic pump, piezoelectric pump peristaltic pump, pneumatic pump, electro-magnetic pump or magnetic pump. A biological pump is formed, e.g. by cardiomyocytes, which are seeded preferably on elastic polymers of a shape supporting pulsate flow at cardiomyocyte contraction (Tanaka et al., 2006, Lab Chip, 6, 362-386). The twitching of the cardiomyocytes provides the contraction necessary for the pumping action. The directionality of the flow, i.e. from the venular channels into the arteriolar channels of the pumping device (5), may be established by the mode of actuation of the pump (5) which leads to the expulsion of fluid only on one side of the pumping device (5) or in cases, wherein the pumping device (5) merely pulsates by further elements that foster a directional flow into the arteriolar channels. Accordingly, in a preferred embodiment the directional pumping device (5) comprises one or more directional flow elements, preferably selected from the group consisting of a jet-like element and a one way valve element. The flow elements may be arranged in the flow path out of the venular transport channel (7) in front of the directional pumping device (5) and/or in the flow path into the arteriolar channel after the directional pumping device (5). In case of jet-like elements it is preferred that they are arranged at both ends of the directional pumping device (5). Preferably the pumping mechanism is based on the pulsations of the preferred elastic PDMS-matrix/membrane actuated by the pumping chamber to generate a continuous peristaltic flow of the medium.

Preferably, the inner surface of said transport channels and/or the directional pumping device (5) is coated with a substance selected from the group consisting of peptides or proteins promoting cell adhesion on biocompatible polymers or a mixture thereof. The adhesion molecules suitable for maintaining the cells are selected from the group consisting of integrins, albumins, fibrins, adhesines and/or collagens, or mixtures thereof. This coating fosters the complete coverage of the inner surface of the circulation system (1) with endothelial cells and/or smooth muscle cells.

In a preferred embodiment of the circulation system (1) of the present invention further comprising capillaries (14) and/or organoids (15) formed in the capillary growth section (2).

Preferably, the capillary growth section (2), the directional pumping device, the arteriolar transport channel(s) (6) and the venular transport channel (7) are made as one piece. The one-piece may be composed of different materials which are adhered to each other. For example the directional pumping device (5), the arteriolar transport channel(s) (6) and the venular transport channel (7) are formed, e.g. by micro-machining or casting, in a block of gas permeable material, e.g. PDMS. The part comprising the capillary growth section and the micro inlets and micro outlets is formed in a non-gas permeable material, which is adhered to the other part in a way that each micro inlet and micro outlet, respectively aligns with an arteriolar transport channel (6) and venular transport channel (7), respectively. As it is also preferred that the matrix (8) and/or hollow fibres which is (are) arranged in the capillary growth section is (are) made from a different material than the capillary growth section, it is preferred that this part is separately produced and inserted into the capillary growth section. Preferably, the capillary growth section is then covered by a non-gas permeable cover unless it serves the function of a microlung.

Preferably, the dimensions of a circulation system (1) of the invention support the continuous circulation of 4-8 µl of whole blood through a system the inner surfaces of which are completely covered with endothelial cells, preferably a mono layer thereof. Preferably this circulation system is configured to provide nutrients for at least two different micro-organoids each of microliter scale over several month of culture. The use of blood, preferably whole blood ascertains a strong buffer system, provides all necessary proteins of the plasma to the tissues, supports oxygen transport through the erythrocytes and provides an immunological activities against contaminating microorganisms through white blood cells.

The present invention provides a method of establishing a circulation system (1), comprising the steps of
  a. seeding endothelial cells into the circulation system (1), and
  b. incubating at least until capillaries (14) have formed in the capillary growth section (2) and/or until an endothelial cell layer has formed in the transport channels and/or until an endothelial cell layer has covered all inner surfaces of the pumping device (5).

Endothelial cells are capable of forming capillaries (14), if placed in an environment that provides a growth scaffold, nutrients and oxygen and optionally angionic factors like FGF and/or Vascular Endothel Cadherine (VEC). Accordingly, the endothelial cells are seeded into the system, preferentially through the access port and are incubated until capillaries (14) are formed, which usually takes between 2 to 10 days, preferably 2 to 6 days depending on the number of endothelial cells seeded, the distance between the micro inlets (3) and micro outlets (4), which are to be connected and the total inner surface of the circulation system (1) of the present invention to be covered with endothelial cells. Typically, in the range of 500 to 5,000 cells are seeded into a system with a total fluid volume in the range of 1 µl to 100 µl, preferably in the range of 5 µl to 50 µl. Naturally arteriolars and venules are composed not only of endothelial cells, but also comprise smooth muscle cells and biocompatible matrices. The smooth muscle cells provide flexibility to the arteriolars and venules and render them impermeable to fluids. Accordingly, in a preferred embodiment of the method further comprises the seeding of smooth muscle cells either prior, concomitantly with or after the endothelial cells. Preferably the ratio of endothelial cells and smooth muscle cells seeded is between 5 to 1 and 0.5 to 1, preferably 2 to 1.

Preferably, the method of the invention further comprises the step of injecting whole blood into the microcirculation once an endothelial cell monolayer has covered all surfaces. During the incubation period the endothelial cells are more likely to form intact capillaries (14), if they are exposed constantly to mechanical forces, therefore preferably step b) is carried out under shear force. The shear forces are created by circulating medium through the circulation system (1) of the present invention. Preferably, the flow at the micro inlet (3) and micro outlets (4) are in the range of 5 to 20 dyn/cm$^2$. To allow adherence of the cells to the inner surface of the circulation system (1) and/or migration to the capillary growth chamber (2) the circulation system (1) is filled with a fluid. Accordingly, in a preferred embodiment the seeding cells are comprised in media, plasma or blood, preferably whole blood. A particular preferred "seeding medium" which is also used during the incubation step leading to the formation of the capillaries (14) contains, e.g. endothelial cell basal medium-2 (EBM-2) supplemented with hydrocortisone, fetal calf serum (FCS), porcine VEGF, human basic fibroblast growth factor (hbFGF), human epidermal growth factor (hEGF), insulin-like growth factor (R3 IGF), ascorbic acid, penicillin, streptomycin if the seeding medium is plasma or blood, it is preferred that these are supplemented with one or more of above indicated substances. To determine whether capillaries (14) have formed in step b) micro sensors (12) and/or visual inspection is used. Suitable micro sensors (12) measure transendothelial electrical resistance (TEER). Preferably, one or more non-endothelial cell types are seeded into the circulation system (1), preferably into the capillary growth section (2) to establish tissues and/or organoids (15) in the capillary growth sections (2). This further cells may be seeded prior to, concomitantly with step a), after step a) or after step b). The tissue types from which the cells are derived are preferably selected from the group consisting of liver, skin, lung, kidney, gut, neuronal, cardiac muscle and/or tumours.

The present invention provides a circulation system (1) producible by the described method, e.g. a circulation system with established cappilaries and or organoids.

The present invention provides the use of the circulation system (1) for monitoring the effect of one or more test compounds and/or for determination the efficacy, side-effects, biosafety, metabolites, mode of action or organ regeneration. Preferably, such testing is carried out by injecting one or more test compounds through the injection port.

Figure 1:
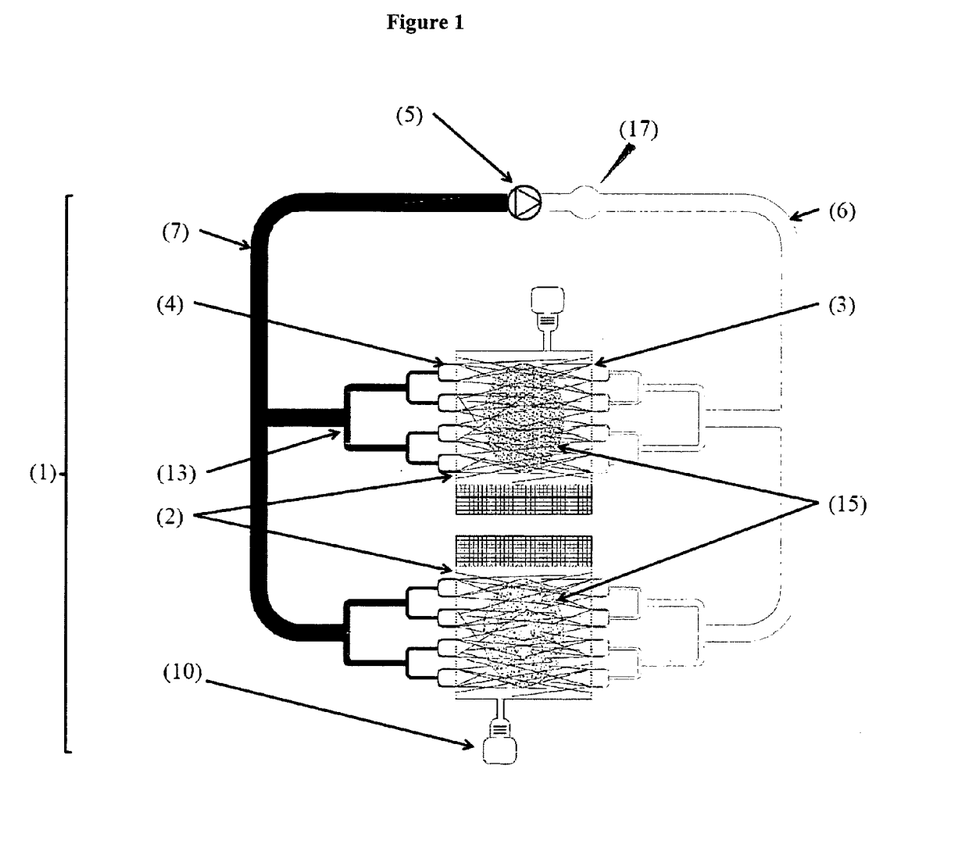
FIG. 1 is a top plan view of a preferred embodiment of a self-contained circulation system.

A top-down view of a preferred embodiment of a self-contained circulation system (1) is shown in FIG. 1, comprising two capillary growth sections (2), the directional pumping device (5) and the arteriolar (6) and venular transport channels (7). In a preferred embodiment the pumping device (5) and the two capillary growth sections (2) are parallel arranged. The transport channels (6, 7) serve as a connection between the directional pumping device (5) and the capillary growth section (2). In a preferred embodiment an injection port (17) for i.e. support of buffer is located in close proximity to the micro pump. Usually, the arteriolar (6) or venular channel (7) connected to the directional pumping device (5) branches of into two or three smaller diameter arteriolar and venular channels at the branching points (13). The capillary growth sections (2) are preferably populated by different tissues and/or organoids (15), which are perfuse by the same circulating fluid and allows, e.g. the testing of the effect of one compound on more than one organoid simultaneously.

Figure 2:
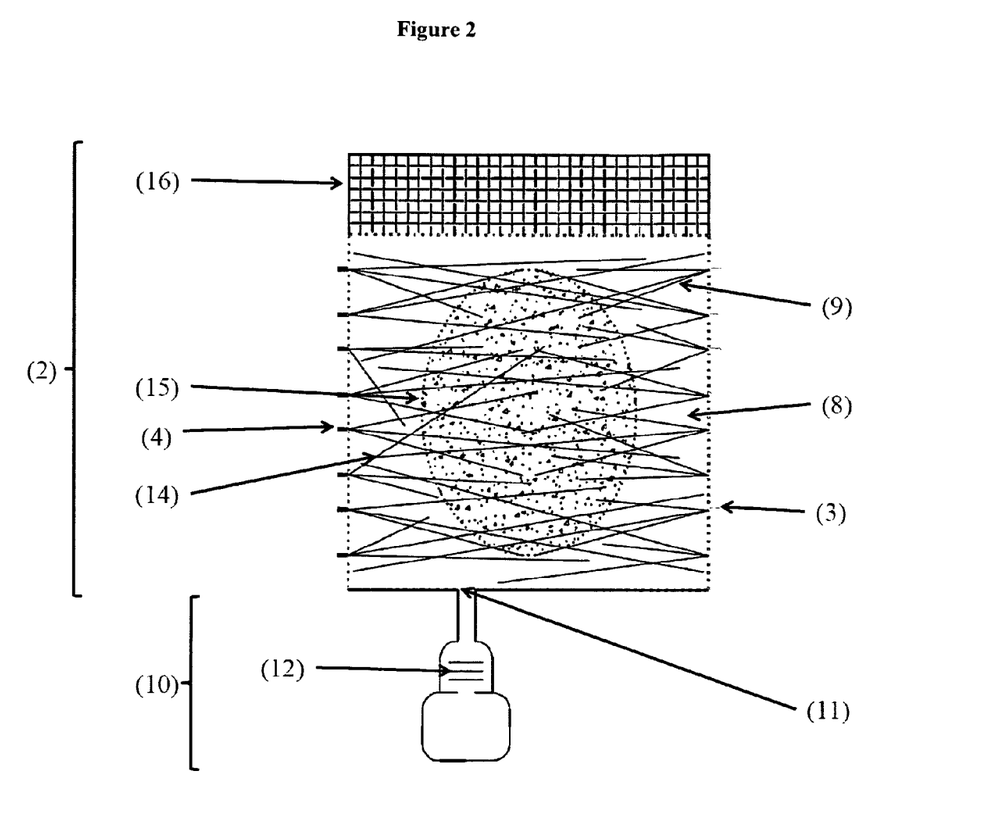
FIG. 2 is top plan view of the capillary growth section (2) of the self-contained circulation system.

A top-down view of a preferred embodiment of the capillary growth section (2) of the self-contained circulation system (1)) is shown in FIG. 2. The capillary growth sections (2) are the spaces that are provided for assembly of capillaries (14) by e.g. endothelial cells between the micro inlets (3) and outlets (4). To provide an appropriate environment for growth of the capillaries (14) it is preferred that the capillary growth section (2) comprises or consists of a semi-solid, biocompatible matrix (8). Alternatively, biocompatible hollow fibres (9) are provided which connected at one side to the micro inlet (3) and at the other side to the micro outlet (4). The tissue site most distant from the inflow end of the capillary (14) builds a neovascularisation region (16) within the capillary growth section (2), i.e. a section wherein no capillaries (14) are formed during the basis establishment of the capillaries (14) in the circulation. Preferably the capillary growth section (2) further comprises an extra-capillary fluid and/or waste collector (10), which is separated from the remaining capillary growth section (2) by a cell retention membrane (11). To monitor the status of the system one or more sensors (12) are arranged in the extra capillary fluid and/or waste collector (10).

Figure 3:
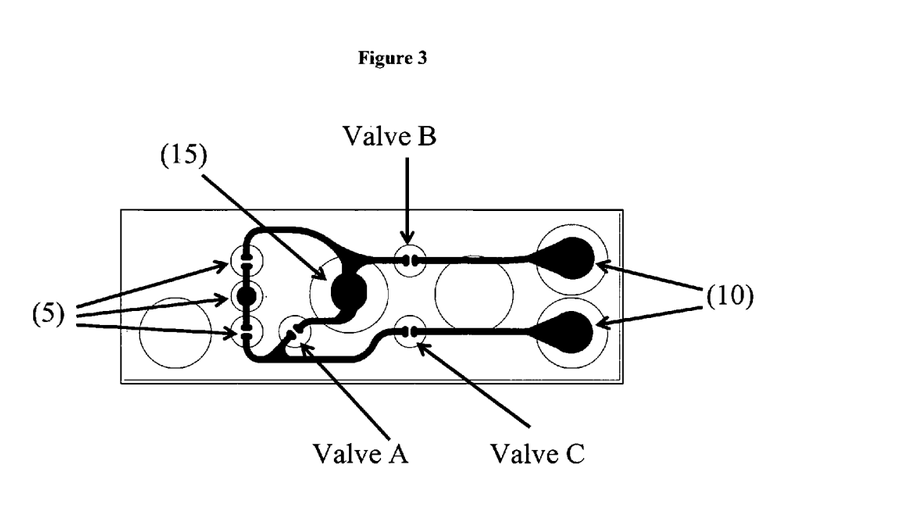
FIG. 3 is top plan view of an alternative preferred embodiment of the self-contained circulation system used in the example experiment.

A top-down view of a preferred embodiment of the self-contained circulation system used in the example experiment is shown in FIG. 3 equipped with a peristaltic pump (5), three valves for liquid displacement, an insert (15) and two collectors (10) supporting fill and flush of the system.

Figure 4:
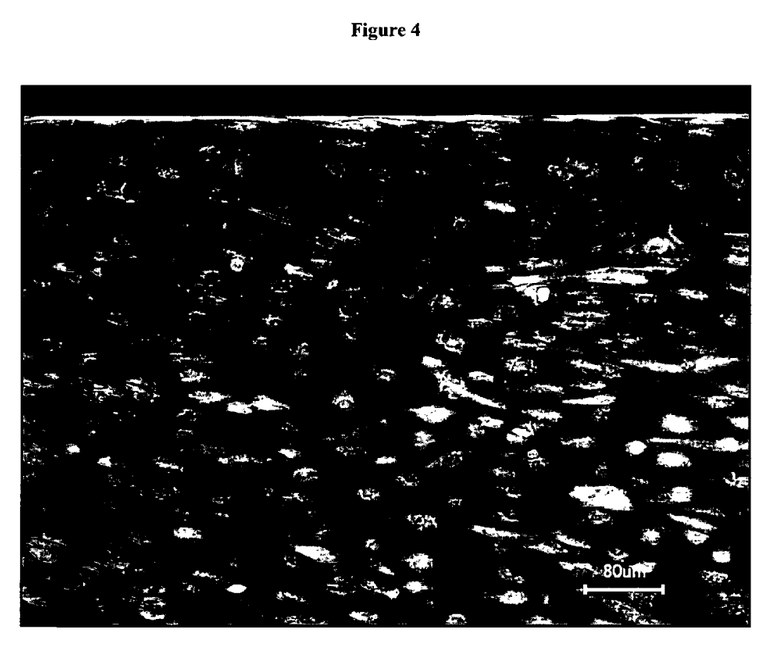
FIG. 4 is a photograph of a CalceinAM viability staining of a particular segment of the channels of the self-contained micro circulation system fully covered with human endothelial cells.

A photograph of a CalceinAM viability staining of a particular segment of the channels of the self-contained micro circulation system fully covered with human endothelial cells after seven days of perfused cultivation is shown in FIG. 4.

Figure 5:
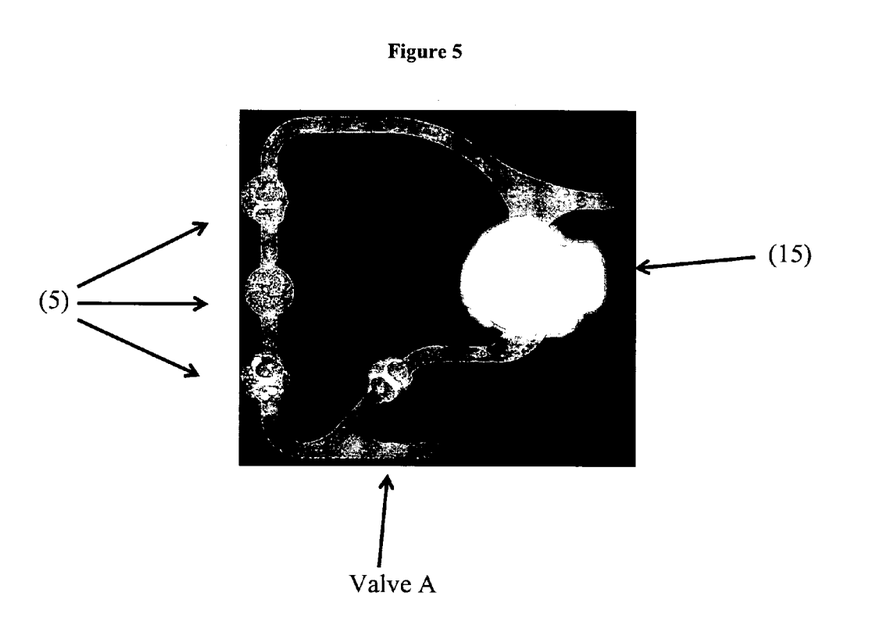
FIG. 5 is a photograph of a CellMask© fluorescent plasma membrane staining of the self-contained circulation system chip fully covered with human endothelial cells.

A photograph of a CellMask© fluorescent plasma membrane staining of the self-contained circulation system chip fully covered with human endothelial cells after seven days of perfusion is shown in FIG. 5.

EXAMPLE

A self-contained circulation system (1) has been established over a period of 14 days by fully covering all channels and Surfaces of a bioreactor prototype chip as shown in FIG. 3 with living human, endothelial cells in sterile medium. A peristaltic micro-pump (5) was used to create the liquid circulation through the tissue culture space (15). The collectors for extra-fluid and waste (10) were used in combination with valves A, B and C to manage the liquid levels and exchange in the system. The chip was casted by using a master and PDMS. The PDMS-layer was then transferred onto a glass slide and was inserted into a holder. Metal inserts for cell and tissue inoculums (15) and extra-fluid or waste collection (10) were fixed to the bioreactor chip through a carbonate plate on the top of the PDMS-slide. A fully assembled self-contained circulation system chip is shown in FIG. 4.

Human dermal microvascular endothelial cells (HDMECs) obtained from Promocell were used between passages 4-7. Prior to use they were grown in T-75 flasks with Endothelial Cell Growth Medium MV-2 (Promocell, 5% FCS, 1% penicillin-streptomycin) at 37° C. and 5% $CO_2$ (humidified incubator) and passaged at 80% confluency. For the experiment, cells were collected by washing once with PBS and adding 2 ml of a 0.25% Trypsin/EDTA solution. Detaching of the cells occurred within 5 min incubation at 37° C. After neutralizing the trypsin solution with 10% FCS in DMEM, cells were centrifuged 5 min at 300×g and counted using a hemocytometer.

A sterile self-contained circulation system chip was flushed with 80% ethanol for minutes. Using a syringe, PBS was then injected into the channels and incubated for another 10 minutes. After replacement of PBS by flushing the channels with HDMEC-Medium, the chip was incubated at 4° C. over night.

For seeding the HDMEC into the microchannels, cell pellet was resuspended in HDMEC-Medium to a final concentration of $2 \times 10^7$ cells/ml. Cell suspension was transferred to the empty insert (FIG. 3, 15). To create a difference in hydrostatic pressure between the insert space and the collectors (FIG. 3, 10), medium from the collectors was removed. The peristaltic pump was then opened to let the cells fill the channels. Additionally, valve A was opened to ensure a homogeneous filling of the whole chip.

To allow attachment and spreading of the endothelial cells on the channel surfaces, the self-contained circulation system chip was incubated at 37° C. and 5% $CO_2$ for 2 h. Afterwards, 50 μl HDMEC-medium was added to the insert and cells were re suspended to fill the channels, in the same manner as described above. Collectors were then filled up with medium, closed tightly and the device was turned upside down to let the cells attach to the ceiling of the channels, too. After 5 h of static incubation the chip was connected to the pneumatic pump device and valve B and C were closed to create a circulating flow. The chip was incubated for 14 days at a pumping frequency of 0.16 Hz and a pressure of 0.3 bar. Medium of the insert and collector space was replaced every day. The effect of shearing on endothelial cell shape and fully closed coverage of all channel surfaces by endothelial cells was determined by fluorescence microscopy (FIGS. 4 and 5).

LIST OF REFERENCE NUMBERS (1) self-contained circulation system
(2) capillary growth section
(3) micro inlet
(4) micro outlet
(5) directional pumping device
(6) arteriolar transport channel
(7) venular transport channel
(8) biocompatible matrix
(9) biocompatible hollow fibre
(10) extra-fluid and/or waste collector
(11) retention membrane or cell exclusion channel
(12) sensors
(13) branching point
(14) capillaries
(15) tissues and/or organoids
(16) neovascularization region
(17) injection port

The invention claimed is:

1. A self-contained fluid circulation system, comprising:
   a. a capillary growth chamber enclosing at least one capillary growth section, the capillary growth chamber having at least two micro inlets and at least two micro outlets which provide and remove fluid from the capillary growth section, the at least one capillary growth section including a tissue culture space oriented between the micro inlets and micro outlets and a neovascularization region adjacent to the tissue culture space remote from the micro inlets and micro outlets,
   b. a directional fluid pumping device having an inlet and an outlet,
   c. an arteriolar transport channel connecting the directional fluid pumping device output and the at least two micro inlets and a venular transport channel connecting the directional fluid pumping device inlet and the at least two micro outlets to form a fluid circulation loop, and
   d. a biocompatible matrix which forms a growth scaffold oriented within the at least one capillary growth section of the capillary growth chamber,
   wherein the fluid in the circulation system passes from the micro inlets through the a biocompatible matrix in the capillary growth section and out through the micro outlets in order to form capillaries within biocompatible matrix,
   wherein the neovascularization region is has a distance from at least 100 μm and up to 500 μm from the micro inlets and/or micro outlets to impair the growth of capillaries.

2. The circulation system of claim 1, wherein the capillary growth chamber has two spaced apart capillary growth sections having two spaced apart sets of the micro inlets and micro outlets feeding two tissue culture spaces.

3. The circulation system of claim 1, wherein the capillary growth chamber is at least in part gas permeable.

4. The circulation system of claim 1, wherein the biocompatible matrix comprises at least one of a semi-solid, biocompatible matrix and semi-solid, biocompatible hollow fibres.

5. The circulation system of claim 4, wherein the biocompatible matrix comprises micro channels, structures and/or networks, which allow formation of capillaries by endothelial cells.

6. The circulation system of claim 1, wherein neovascularization region is devoid of micro inlets and outlets.

7. The circulation system of claim 1, wherein the capillary growth chamber further comprises an extra-capillary fluid and/or waste collector.

8. The circulation system of claim 7, wherein the extra-capillary fluid and/or waste collector is separated from the biocompatible matrix and/or biocompatible hollow fibre by a cell retention membrane or by cell exclusion channels.

9. The circulation system of claim 8, wherein at least one sensor is arranged in the extra capillary fluid and/or waste collector.

10. The circulation system according to claim 1, further comprising capillaries and/or organoids formed in the capillary growth section.

11. The circulation system according to claim 1, wherein two or more different tissues and/or organoids are maintained within one self-contained system, which are perfused by the same circulating fluid.

12. The circulation system according to claim 1, wherein the sub-section space is sufficiently far removed from corresponding micro inlets and micro outlets such that the formation of capillaries is impaired in this sub-section during the initial establishment of capillaries in the capillary growth section.

13. The circulation system according to claim 1, wherein the neovascularization region has a distance from at least 100 μm and up to 300 μm from the micro inlets and/or micro outlets.

14. The circulation system according to claim 1, wherein the arteriolar transport channel branches of at least once to connect with the at least two inlets, and the venular transport channel branches of at least once to connect with the at least two outlets, respectively.

15. The circulation system of claim 14, wherein the combined cross-sectional area of the arteriolar channels after the branching point is essentially identical to the cross-sectional area of the arteriolar channel in front of the branching point and/or the combined cross-sectional area of the venular transport channels after the branching point is essentially identical to the cross-sectional area of the venular channel in front of the branching point.

16. The circulation system of claim 14, wherein the combined cross-sectional area of all inlets is essentially identical to the cross-sectional area of said arteriolar channel and/or arteriolar channels and the combined cross-sectional area of all outlets is essentially identical to the cross-sectional area of said venular channel and/or venular channels, preferably are the cross-sectional areas of arteriolar and venular channels identical.

17. The circulation system according to claim 1, wherein the arteriolar transport channel is gas permeable.

18. The circulation system according to claim 1, wherein the a capillary growth chamber is provided with a removable translucent cover to allow microscopic inspection of the capillary growth in the biocompatible matrix and to facilitate the placement of tissue in the biocompatible matrix in the space adjacent to the capillary growth section having impaired capillary growth.

19. A method of establishing a circulation system according to claim 1, comprising the steps of
   a. seeding endothelial cells into the circulation system, and b. incubating at least until capillaries have formed in the capillary growth section and/or until an endothelial cell layer has formed in the transport channels and/or until an endothelial cell layer has covered all inner surfaces of the pumping device.

20. The method of establishing a circulation system according to claim 19, wherein the method further comprises the step of injecting whole blood into said circulation system.

21. The method of establishing a circulation system according to claim 19, wherein step b) is carried out under shear force.

* * * * *

UNITED STATES PATENT AND TRADEMARK OFFICE
CERTIFICATE OF CORRECTION

PATENT NO.           : 9,506,024 B2                                           Page 1 of 1
APPLICATION NO.      : 13/814673
DATED                : November 29, 2016
INVENTOR(S)          : Uwe Marx et al.

It is certified that error appears in the above-identified patent and that said Letters Patent is hereby corrected as shown below:

In the Claims

Column 15, Line 50, Claim 1:
After "micro inlets through the"
Delete "a".

Column 15, Line 54, Claim 1:
After "neovascularization region"
Delete "is".

Column 16, Line 35, Claim 14:
After "transport channel branches"
Delete "of" and
Insert -- off --.

Column 16, Line 37, Claim 14:
After "transport channel branches"
Delete "of" and
Insert -- off --.

Column 16, Line 58, Claim 18:
After "claim 1, wherein the"
Delete "a".

Signed and Sealed this
Twenty-first Day of March, 2017

Michelle K. Lee
*Director of the United States Patent and Trademark Office*